United States Patent [19]

Shaw et al.

[11] Patent Number: 5,693,801
[45] Date of Patent: Dec. 2, 1997

[54] CERTAIN ARYL AND CYCLOALKYL FUSED IMIDAZOPYRAZINEDIONES; A NEW CLASS OF GABA BRAIN RECEPTOR LIGANDS

[75] Inventors: Kenneth Shaw, Weston; Alan Hutchison, Madison, both of Conn.

[73] Assignee: Neurogen Corporation, Branford, Conn.

[21] Appl. No.: 331,561

[22] PCT Filed: Apr. 30, 1993

[86] PCT No.: PCT/US93/03918

§ 371 Date: Oct. 28, 1994

§ 102(e) Date: Oct. 28, 1994

[87] PCT Pub. No.: WO93/22314

PCT Pub. Date: Nov. 11, 1993

Related U.S. Application Data

[63] Continuation of Ser. No. 876,502, Apr. 30, 1992, Pat. No. 5,266,698.

[51] Int. Cl.$^6$ .............. C07D 487/04; C07D 471/14; C07D 495/14; C07D 487/14

[52] U.S. Cl. .............................................. 544/346

[58] Field of Search ............................... 544/346

[56] References Cited

U.S. PATENT DOCUMENTS 5,130,430  7/1992  Shaw ........................ 544/346

FOREIGN PATENT DOCUMENTS 92-7853  5/1992  WIPO .

OTHER PUBLICATIONS

Occelli et al. *Il Farmaco*, 39, 322(1984).

Primary Examiner—Mark L. Berch
Attorney, Agent, or Firm—McDonnell Boehnen Hulbert & Berghoff

[57] ABSTRACT

Disclosed are compounds of the formula:

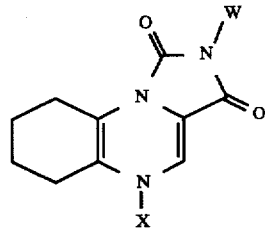

or the pharmaceutically acceptable salts thereof wherein:

X is hydrogen or lower alkyl having 1–6 carbon atoms; and

W is an optionally substituted aryl group as defined herein.

21 Claims, 1 Drawing Sheet

Compound 1

Compound 5

Compound 8

CERTAIN ARYL AND CYCLOALKYL FUSED IMIDAZOPYRAZINEDIONES; A NEW CLASS OF GABA BRAIN RECEPTOR LIGANDS

This application is a national phase application filed pursuant to 35 U.S.C. §371 of International Application No. PCT/US93/03918 filed Apr. 30, 1993, which is a continuation of U.S. application Ser. No. 07/876,502 filed Apr. 30, 1992, now U.S. Pat. No. 5,266,698.

BACKGROUND OF THE INVENTION

1. Field of the Invention

This invention relates to certain aryl and cycloalkyl fused imidazopyrazinediones which selectively bind to GABAa receptors. This invention also relates to pharmaceutical compositions comprising such compounds. It further relates to the use of such compounds in treating anxiety, sleep and seizure disorders, and overdoses of benzodiazepine-type drugs, and enhancing alertness. The interaction of aryl and cycloalkyl fused imidazopyrazinediones of the invention with a GABA binding site, the benzodiazepines (BDZ) receptor, is described. This interaction results in the pharmacological activities of these compounds.

2. Description of the Related Art

γ-Aminobutyric acid (GABA) is regarded as one of the major inhibitory amino acid transmitters in the mammalian brain. Over 30 years have elapsed since its presence in the brain was demonstrated (Roberts & Frankel, J. Biol. Chem 187: 55–63, 1950; Udenfriend, J. Biol. Chem. 187: 65–69, 1950). Since that time, an enormous amount of effort has been devoted to implicating GABA in the etiology of seizure disorders, sleep, anxiety and cognition (Tallman and Gallager, Ann. Rev. Neuroscience 8: 21–44, 1985). Widely, although unequally, distributed through the mammalian brain, GABA is said to be a transmitter at approximately 30% of the synapses in the brain. In most regions of the brain, GABA is associated with local inhibitory neurons and only in two regions is GABA associated with longer projections. GABA mediates many of its actions through a complex of proteins localized both on cell bodies and nerve endings; these are called GABAa receptors. Postsynaptic responses to GABA are mediated through alterations in chloride conductance that generally, although not invariably, lead to hyperpolarization of the cell. Recent investigations have indicated that the complex of proteins associated with postsynaptic GABA responses is a major site of action for a number of structurally unrelated compounds capable of modifying postsynaptic responses to GABA. Depending on the mode of interaction, these compounds are capable of producing a spectrum of activities (either sedative, anxiolytic, and anticonvulsant, or wakefulness, seizures, and anxiety).

1,4-Benzodiazepines continue to be among the most widely used drugs in the world. Principal among the benzodiazepines marketed are chlordiazepoxide, diazepam, flurazepam, and triazolam. These compounds are widely used as anxiolytics, sedative-hypnotics, muscle relaxants, and anticonvulsants. A number of these compounds are extremely potent drugs; such potency indicates a site of action with a high affinity and specificity for individual receptors. Early electrophysiological studies indicated that a major action of benzodiazepines was enhancement of GABAergic inhibition. The benzodiazepines were capable of enhancing presynaptic inhibition of a monosynaptic ventral root reflex, a GABA-mediated event (Schmidt et al., 1967, Arch. Exp. Path. Pharmakol. 258: 69–82). All subsequent electrophysiological studies (reviewed in Tallman et al. 1980, Science 207:274–81, Haefley et al., 1981, Handb. Exptl. Pharmacol. 33: 95–102) have generally confirmed this finding, and by the mid-1970s, there was a general consensus among electrophysiologists that the benzodiazepines could enhance the actions of GABA.

With the discovery of the "receptor" for the benzodiazepines and the subsequent definition of the nature of the interaction between GABA and the benzodiazepines, it appears that the behaviorally important interactions of the benzodiazepines with different neurotransmitter systems are due in a large part to the enhanced ability of GABA itself to modify these systems. Each modified system, in turn, may be associated with the expression of a behavior.

Studies on the mechanistic nature of these interactions depended on the demonstration of a high-affinity benzodiazepine binding site (receptor). Such a receptor is present in the CNS of all vertebrates phylogenetically newer than the boney fishes (Squires & Braestrup 1977, Nature 166: 732–34, Mohler & Okada, 1977, Science 198: 854–51, Mohler & Okada, 1977, Br. J. Psychiatry 133: 261–68). By using tritiated diazepam, and a variety of other compounds, it has been demonstrated that these benzodiazepine binding sites fulfill many of the criteria of pharmacological receptors; binding to these sites in vitro is rapid, reversible, stereospecific, and saturable. More importantly, highly significant correlations have been shown between the ability of benzodiazepines to displace diazepam from its binding site and activity in a number of animal behavioral tests predictive of benzodiazepine potency (Braestrup & Squires 1978, Br. J. Psychiatry 133: 249–60, Mohler & Okada, 1977, Science 198: 854–51, Mohler & Okada, 1977, Br. J. Psychiatry 133: 261–68). The average therapeutic doses of these drugs in man also correlate with receptor potency (Tallman et al. 1980, Science 207: 274–281).

In 1978, it became clear that GABA and related analogs could interact at the low affinity (1 mM) GABA binding site to enhance the binding of benzodiazepines to the clonazepam-sensitive site (Tallman et al. 1978, Nature, 274: 383–85). This enhancement was caused by an increase in the affinity of the benzodiazepine binding site due to occupancy of the GABA site. The data were interpreted to mean that both GABA and benzodiazepine sites were allosterically linked in the membrane as part of a complex of proteins. For a number of GABA analogs, the ability to enhance diazepam binding by 50% of maximum and the ability to inhibit the binding of GABA to brain membranes by 50% could be directly correlated. Enhancement of benzodiazepine binding by GABA agonists is blocked by the GABA receptor antagonist (+) bicuculline; the stereoisomer (−) bicuculline is much less active (Tallman et al., 1978, Nature, 274: 383–85).

Soon after the discovery of high affinity binding sites for the benzodiazepines, it was discovered that a triazolopyridazine could interact with benzodiazepine receptors in a number of regions of the brain in a manner consistent with receptor heterogeneity or negative cooperativity. In these studies, Hill coefficients significantly less than one were observed in a number of brain regions, including cortex, hippocampus, and striatum. In cerebellum, triazolopyridazine interacted with benzodiazepine sites with a Hill coefficient of 1 (Squires et al., 1979, Pharma. Biochem. Behav. 10: 825–30, Klepner et al. 1979, Pharmacol. Biochem. Behav. 11: 457–62). Thus, multiple benzodiazepine receptors were predicted in the cortex, hippocampus, striatum, but not in the cerebellum.

Based on these studies, extensive receptor autoradiographic localization studies were carried out at a light microscopic level. Although receptor heterogeneity has been demonstrated (Young & Kuhar 1980, J. Pharmacol. Exp. Ther. 212: 337–46. Young et al., 1981 J. Pharmacol Exp. ther 216: 425–430, Niehoff et al. 1982, J. Pharmacol. Exp. Ther. 221: 670–75), no simple correlation between localization of receptor subtypes and the behaviors associated with the region has emerged from the early studies. In addition, in the cerebellum, where one receptor was predicted from binding studies, autoradiography revealed heterogeneity of receptors (Niehoff et al., 1982, J. Pharmacol. Exp. Ther. 221: 670–75).

A physical basis for the differences in drug specificity for the two apparent subtypes of benzodiazepine sites has been demonstrated by Sieghart & Karobath, 1980, Nature 286: 285–87. Using gel electrophoresis in the presence of sodium dodecyl sulfate, the presence of several molecular weight receptors for the benzodiazepines has been reported. The receptors were identified by the covalent incorporation of radioactive flunitrazepam, a benzodiazepine which can covalently label all receptor types. The major labeled bands have molecular weights of 50,000 to 53,000, 55,000, and 57,000 and the triazolopyridazines inhibit labeling of the slightly higher molecular weight forms (53,000, 55,000, 57,000) (Seighart et al. 1983, Eur. J. Pharmacol. 88: 291–99).

At that time, the possibility was raised that the multiple forms of the receptor represent "isoreceptors" or multiple allelic forms of the receptor (Tallman & Gallager 1985, Ann. Rev. Neurosci. 8, 21–44). Although common for enzymes, genetically distinct forms of receptors have not generally been described. As we begin to study receptors using specific radioactive probes and electrophoretic techniques, it is almost certain that isoreceptors will emerge as important in investigations of the etiology of psychiatric disorders in people.

The GABAa receptor subunits have been cloned from bovine and human cDNA libraries (Schoenfield et al., 1988; Duman et al., 1989). A number of distinct cDNAs were identified as subunits of the GABAa receptor complex by cloning and expression. These are categorized into α, β, γ, δ, ε, and provide a molecular basis for the GABAa receptor heterogeneity and distinctive regional pharmacology (Shivvers et al., 1980; Levitan et al., 1989). The g subunit appears to enable drugs like benzodiazepines to modify the GABA responses (Pritchett et al., 1989). The presence of low Hill coefficients in the binding of ligands to the GABAa receptor indicates unique profiles of subtype specific pharmacological action.

Drugs that interact at the GABAa receptor can possess a spectrum of pharmacological activities depending on their abilities to modify the actions of GABA. For example, the beta-carbolines were first isolated based upon their ability to inhibit competitively the binding of diazepam to its binding site (Nielsen et al., 1979, Life Sci. 25: 679–86). The receptor binding assay is not totally predictive about the biological activity of such compounds; agonists, partial agonists, inverse agonists, and antagonists can inhibit binding. When the beta-carboline structure was determined, it was possible to synthesize a number of analogs and test these compounds behaviorally. It was immediately realized that the beta-carbolines could antagonize the actions of diazepam behaviorally (Tenen & Hirsch, 1980, Nature 288: 609–10). In addition to this antagonism, beta-carbolines possess intrinsic activity of their own opposite to that of the benzodiazepines; they become known as inverse agonists.

In addition, a number of other specific antagonists of the benzodiazepine receptor were developed based on their ability to inhibit the binding of benzodiazepines. The best studied of these compounds is an imidazodiazepine (Hunkeler et al., 1981, Nature 290: 514–516). This compound is a high affinity competitive inhibitor of benzodiazepine and betacarboline binding and is capable of blocking the pharmacological actions of both these classes of compounds. By itself, it possesses little intrinsic pharmacological activity in animals and humans (Hunkeler et al., 1981, Nature 290: 514–16; Darragh et al., 1983, Eur. J. Clin. Pharmacol. 14: 569–70). When a radiolabeled form of this compound was studied (Mohler & Richards, 1981, Nature 294: 763–65), it was demonstrated that this compound would interact with the same number of sites as the benzodiazepines and betacarbolines, and that the interactions of these compounds were purely competitive. This compound is the ligand of choice for binding to GABAa receptors because it does not possess receptor subtype specificity and measures each state of the receptor.

The study of the interactions of a wide variety of compounds similar to the above has led to the categorizing of these compounds. Presently, those compounds possessing activity similar to the benzodiazepines are called agonists. Compounds possessing activity opposite to benzodiazepines are called inverse agonists, and the compounds blocking both types of activity have been termed antagonists. This categorization has been developed to emphasize the fact that a wide variety of compounds can produce a spectrum of pharmacological effects, to indicate that compounds can interact at the same receptor to produce opposite effects, and to indicate that beta-carbolines and antagonists with intrinsic anxiogenic effects are not synonymous.

A biochemical test for the pharmacological and behavioral properties of compounds that interact with the benzodiazepine receptor continues to emphasize the interaction with the GABAergic system. In contrast to the benzodiazepines, which show an increase in their affinity due to GABA (Tallman et al., 1978, Nature 274: 383–85, Tallman et al., 1980, Science 207: 274–81), compounds with antagonist properties show little GABA shift (i.e., change in receptor affinity due to GABA) (Mohler & Richards 1981, Nature 294: 763–65), and the inverse agonists actually show a decrease in affinity due to GABA (Braestrup & Nielson 1981, Nature 294: 472–474). Thus, the GABA shift predicts generally the expected behavioral properties of the compounds.

Various compounds have been prepared as benzodiazepine agonists and antagonists. For example, U.S. Pat. Nos. 4,312,870 and 4,713,383, and European Patent Application EP 181,282 disclose assorted compounds useful in treating anxiety or depression. U.S. Patent No. 4,713,383 teaches compounds of the formula:

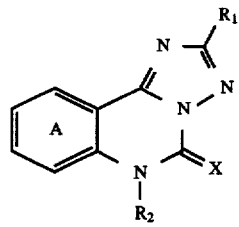

wherein $R_1$=(un)substituted Ph, (dihydro)furanyl, tetrahydrofuranyl, (dihydro)thienyl, tetrahydrothienyl, pyranyl, ribofuranosyl, all C-attached; $R_2$=H, alkyl; X=O, S, $R_3N$; $R_3$=H, alkenyl, alkynyl, $C_{3-20}$ cycloalkyl, (un)substituted alkyl, aryl, aralkyl, where aryl is Ph, pyridinyl, thienyl, furanyl; ring A may be substituted by alkyl, alkoxy, halo, amino, alkylthio, etc.

European Patent Application EP 181,282 discloses compounds of the formula:

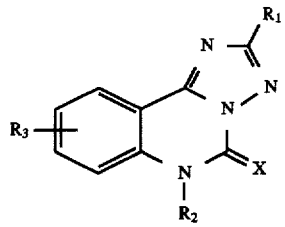

wherein $R_1$=(substituted) Ph or heterocycle; $R_2$=H, alkyl, alkenyl, hydroxyalkyl, aralkyl, aralkenyl, aryl; $R_3$=H, alkyl, alkoxy, HO, halo, $F_3C$, $O_3N$, $H_2N$, alkylthio, alkylsulfinyl, alkylsulfonyl, aralkoxy; X=O, S, $NR_4$; and $R_4$=H, alkyl, aralkyl, cycloalkyl, alkenyl, alkynyl, aryl, (substituted) aminoaklyl, hydroxyalkyl.

U.S. Pat. No. 4,312,870 teaches compounds of formulas:

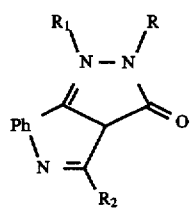

and

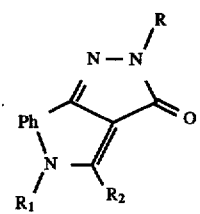

where Ph is 1,2-phenylene, unsubstituted or substituted by up to 3 identical or different members selected from lower alkyl, lower alkoxy, lower alkylthio, hydroxy, halogeno, trifluoromethyl, nitro, amino, mono- or di-lower alkylamino, cyano, carbamoyl and carboxy; R is unsubstituted or substituted phenyl as defined by H-Ph, pyridyl, lower alkylpyridyl, or halogenopyridyl; $R_1$ is hydrogen, lower alkyl or lower (hydroxy, dialkylamino or H-Ph)-alkyl; and $R_2$ is hydrogen or lower alkyl alkyl; their 3-hydroxy-tautomers; lower alkanoyl, carbamoyl, mono- or di-lower alkyl-carbamoyl derivatives of said (hydroxy or amino)-(phenyl or phenylene) compounds: and

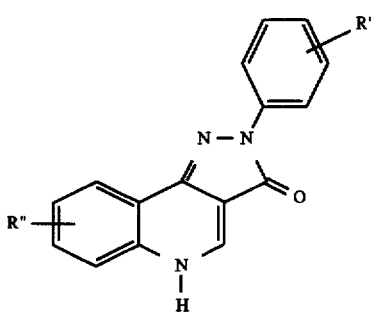

where R" is hydrogen, alkyl or alkoxy with up to 4 carbon atoms each, hydroxy, fluoro, chloro, bromo, or trifluoromethyl; and R' is hydrogen, o- or m-fluoro; or it is p-fluoro when R" is chloro.

The compounds of the present invention differ from these compounds. These compounds are not imidazopyrazines and lack the various ring substituents of the compounds of the present invention.

SUMMARY OF THE INVENTION

This invention provides novel compounds of Formula I which interact with a GABAa binding site, the benzodiazepine receptor.

The invention provides pharmaceutical compositions comprising compounds of Formula I. The invention also provides compounds useful in enhancing alertness, treatment of seizure, anxiety, and sleep disorders, and treatment of benzodiazepine overdoses. Accordingly, a broad embodiment of the invention is directed to compounds of Formula I:

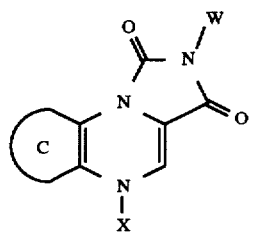

and the pharmaceutically acceptable non-toxic salts thereof wherein:

X is hydrogen or lower alkyl having 1–6 carbon atoms;
W is phenyl, thienyl, or pyridyl:
  phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

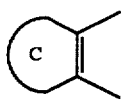

represents

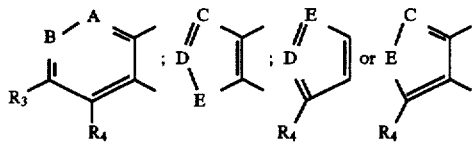

wherein:

A represents nitrogen or C—R$_1$;

B represents nitrogen or C—R$_2$ with the proviso that not both A and B are nitrogen;

C represents nitrogen or C—R$_1$;

D represents nitrogen or C—R$_2$ with the proviso that not both C and D are nitrogen;

E represents oxygen, sulfur or N—R$_5$;

R$_1$ and R$_4$ are the same or different and represent hydrogen, halogen, straight or branched chain lower alkyl having 1–6 carbon atoms, or straight or branched chain lower alkoxy having 1–6 carbon atoms;

R$_2$ is hydrogen, halogen, hydroxy, amino, 1-indanyl, 4-(thio)chromanyl, 1-(1,2,3,4-tetrahydronaphthyl);

1-indanyl, 4-(thio)chromanyl, 1-(1,2,3,4-tetrahydronaphthyl), each of which is monosubstituted with halogen, straight or branched chain lower alkyl having 1–6, carbon atoms, or straight or branched chain lower alkoxy having 1–6 carbon atoms;

OR$_5$, COR$_5$, CO$_2$R$_5$, OCOR$_5$, or R$_5$, where R$_5$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms;

—CONR$_6$R$_7$ or —(CH$_2$)$_n$NR$_6$R$_7$ where n is 0, 1, or 2;

R$_6$ is hydrogen, straight or branched chain lower alkyl having 1–6 carbon atoms; and R$_7$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or NR$_6$R$_7$ forms a heterocyclic group which is morpholyl, piperidyl, pyrrolidyl, or N-alkyl piperazyl; or C(OH)R$_{10}$R$_{11}$ where R$_{10}$ and R$_{11}$ are the same or different and represent straight or branched chain lower alkyl having 1–6 carbon atoms, phenyl, or phenylalkyl where each alkyl is straight or branched chain lower alkyl having 1–6 carbon atoms; and R$_3$ and R$_5$ are the same or different and represent hydrogen or straight or branched chain lower alkyl having 1–6 carbon atoms; or

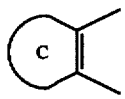

represents

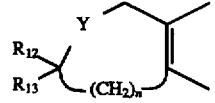

where n is 0, 1 or 2;

R$_{12}$ and R$_{13}$ are the same or different and represent hydrogen or straight chain or branched lower alkyl having 1–6 carbon atoms;

Y is N—R$_{14}$ where R$_{14}$ is hydrogen, phenyl, pyridyl, straight or branched chain lower alkyl having 1–6 carbon atoms, phenylalkyl or pyridylalkyl where each alkyl is straight or branched chain lower alkyl having 1–6 carbon atoms;

aminoalkyl where the alkyl is a straight or branched chain lower alkyl having 1–6 carbon atoms, or mono or dialkyl aminoalkyl where each alkyl is a straight or branched chain lower alkyl having 1–6 carbon atoms;

1-indanyl, 4-(thio)chromanyl, 1-(1,2,3,4-tetrahydronaphthyl);

1-indanyl, 4-(thio)chromanyl, 1-(1,2,3,4-tetrahydronaphthyl) each of which is monosubstituted with halogen, straight or branched chain lower alkyl having 1–6 carbon atoms, or straight or branched chain lower alkoxy having 1–6 carbon atoms;

—COR$_{15}$ or —SO$_2$R$_{15}$ where R$_{15}$ is straight or branched chain lower alkyl having 1–6 carbon atoms, phenyl, pyridyl, phenylalkyl or pyridylalkyl where each alkyl is straight or branched chain lower alkyl having 1–6 carbon atoms, or phenylalkoxy or pyridylalkoxy where each alkoxy is straight or branched chain lower alkoxy having 1–6 carbon atoms;

—CO—, —CR$_{17}$OR$_{16}$, —CR$_{17}$COR$_{16}$, —CR$_{17}$CO$_2$R$_{16}$, —CR$_{17}$OCOR$_{16}$, and —CR$_{16}$R$_{17}$, where R$_{16}$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms, and R$_{17}$ is hydrogen, or straight or branched chain lower alkyl having 1–6 carbon atoms;

—CR$_{17}$CONR$_{18}$R$_{19}$ or —CR$_{17}$(CH$_2$)$_n$NR$_{18}$R$_{19}$ where n is 0, 1, or 2, and R$_{17}$ and R$_{18}$ are the same or different and represent hydrogen, straight or branched chain lower alkyl having 1–6 carbon atoms, and R$_{19}$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms, or NR$_{18}$R$_{19}$ together forms a heterocyclic group which is morpholyl, piperidyl, pyrrolidyl, or N-alkylpiperazyl;

—$CR_{17}NR_{20}CO_2R_{21}$ where $R_{17}$ is hydrogen, straight or branched chain lower alkyl having 1–6 carbon atoms, and $R_{20}$ and $R_{21}$ are the same or different and represent hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms;

—$CR_{17}C(OH)R_{22}R_{23}$ where $R_{22}$ and $R_{23}$ are the same or different and represent straight or branched chain lower alkyl having 1–6 carbon atoms, phenyl, pyridyl, straight or branched chain lower alkyl having 1–6 carbon atoms, or phenylalkyl or pyridylalkyl where each alkyl is straight or branched chain lower alkyl having 1–6 carbon atoms and $R_{17}$ is hydrogen, or straight or branched chain lower alkyl having 1–6 carbon atoms;

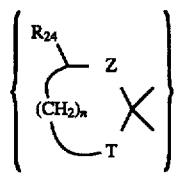

where n is 0, 1, or 2, $R_{24}$ is hydrogen, aryl, heteroaryl, straight or branched chain lower alkyl having 1–6 carbon atoms, or aryl or heteroaryl straight or branched chain lower alkyl having 1–carbon atoms;

Z is methylene, oxygen, $NR_{25}$ or —$CHCONR_{25}$ where $R_{25}$ is hydrogen, straight or branched chain lower alkyl having 1–6 carbon atoms, phenyl, pyridyl, or phenylalkyl or pyridyl alkyl where each alkyl is straight or branched chain lower alkyl having 1–6 carbon atoms; and T is methylene or oxygen.

These compounds are highly selective agonists, antagonists or inverse agonists for GABAa brain receptors or prodrugs of agonists, antagonists or inverse agonists for GABAa brain receptors. These compounds are useful in the diagnosis and treatment of anxiety, sleep, and seizure disorders, overdose with benzodiazepine drugs, and enhancement of memory.

DETAILED DESCRIPTION OF THE INVENTION

Figure 1A:
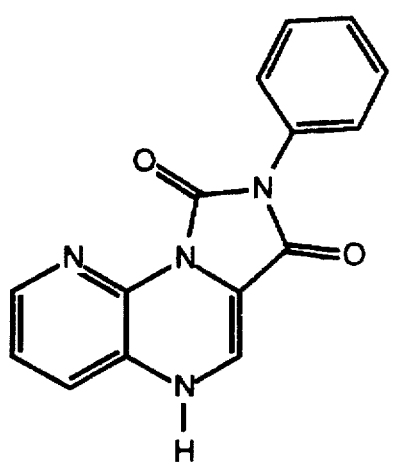
FIGS. 1A–C show representative aryl and cycloalkyl fused imidazopyrazinediones of the present invention.

The novel compounds encompassed by the instant invention can be described by the following general formula I:

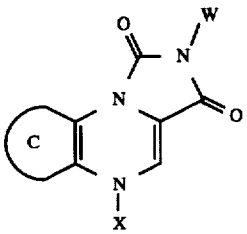

and the pharmaceutically acceptable non-toxic salts thereof wherein:

X is hydrogen or lower alkyl having 1–6 carbon atoms:

W is phenyl, thienyl, or pyridyl;

phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

represents

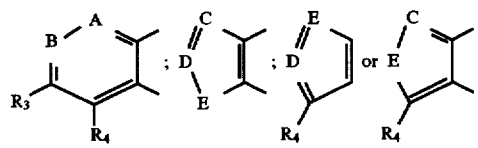

wherein:

A represents nitrogen or C—$R_1$;

B represents nitrogen or C—$R_2$ with the proviso that not both A and B are nitrogen;

C represents nitrogen or C—$R_1$;

D represents nitrogen or C—$R_2$ with the proviso that not both C and D are nitrogen;

E represents oxygen, sulfur or N—$R_5$;

$R_1$ and $R_4$ are the same or different and represent hydrogen, halogen, straight or branched chain lower alkyl having 1–6 carbon atoms, or straight or branched chain lower alkoxy having 1–6 carbon atoms;

$R_2$ is hydrogen, halogen, hydroxy, amino, 1-indanyl, 4-(thio)chromanyl, 1-(1,2,3,4-tetrahydronaphthyl);

1-indanyl, 4-(thio)chromanyl, 1-(1,2,3,4-tetrahydronaphthyl), each of which is monosubstituted with halogen, straight or branched chain lower alkyl having 1–6. carbon atoms, or straight or branched chain lower alkoxy having 1–6 carbon atoms;

$OR_5$, $COR_5$, $CO_2R_5$, $OCOR_5$, or $R_5$, where $R_5$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms;

—$CONR_6R_7$ or —$(CH_2)_nNR_6R_7$ where n is 0, 1, or 2;

$R_6$ is hydrogen, straight or branched chain lower alkyl having 1–6 carbon atoms; and $R_7$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or $NR_6R_7$ forms a heterocyclic group which is morpholyl, piperidyl, pyrrolidyl, or N-alkyl piperazyl; or $C(OH)R_{10}R_{11}$ where $R_{10}$ and $R_{11}$ are the same or different and represent straight or branched chain lower alkyl having 1–6 carbon atoms, phenyl, or phenylalkyl where each alkyl is straight or branched chain lower alkyl having 1–6 carbon atoms; and $R_3$ and $R_5$ are the same or different and represent hydrogen or straight or branched chain lower alkyl having 1–6 carbon atoms; or

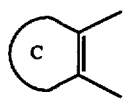

represents

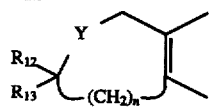

where
n is 0, 1 or 2;

$R_{12}$ and $R_{13}$ are the same or different and represent hydrogen or straight chain or branched lower alkyl having 1–6 carbon atoms;

Y is N—$R_{14}$ where $R_{14}$ is hydrogen, phenyl, pyridyl, straight or branched chain lower alkyl having 1–6 carbon atoms, phenylalkyl or pyridylalkyl where each alkyl is straight or branched chain lower alkyl having 1–6 carbon atoms;

aminoalkyl where the alkyl is a straight or branched chain lower alkyl having 1–6 carbon atoms, or mono or dialkyl aminoalkyl where each alkyl is a straight or branched chain lower alkyl having 1–6 carbon atoms;

1-indanyl, 4-(thio)chromanyl, 1-(1,2,3,4-tetrahydronaphthyl);

1-indanyl, 4-(thio)chromanyl, 1-(1,2,3,4-tetrahydronaphthyl) each of which is monosubstituted with halogen, straight or branched chain lower alkyl having 1–6 carbon atoms, or straight or branched chain lower alkoxy having 1–6 carbon atoms;

—$COR_{15}$ or —$SO_2R_{15}$ where $R_{15}$ is straight or branched chain lower alkyl having 1–6 carbon atoms, phenyl, pyridyl, phenylalkyl or pyridylalkyl where each alkyl is straight or branched chain lower alkyl having 1–6 carbon atoms, or phenylalkoxy or pyridylalkoxy where each alkoxy is straight or branched chain lower alkoxy having 1–6 carbon atoms;

—CO—, —$CR_{17}OR_{16}$, —$CR_{17}COR_{16}$, —$CR_{17}CO_2R_{16}$, —$CR_{17}OCOR_{16}$, and —$CR_{16}R_{17}$, where $R_{16}$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms, and $R_{17}$ is hydrogen, or straight or branched chain lower alkyl having 1–6 carbon atoms;

—$CR_{17}CONR_{18}R_{19}$ or —$CR_{17}(CH_2)_nNR_{18}R_{19}$ where n is 0, 1, or 2, and $R_{17}$ and $R_{18}$ are the same or different and represent hydrogen, straight or branched chain lower alkyl having 1–6 carbon atoms, and $R_{19}$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms, or $NR_{18}R_{19}$ together forms a heterocyclic group which is morpholyl, piperidyl, pyrrolidyl, or N-alkylpiperazyl;

—$CR_{17}NR_{20}CO_2R_{21}$ where $R_{17}$ is hydrogen, straight or branched chain lower alkyl having 1–6 carbon atoms, and $R_{20}$ and $R_{21}$ are the same or different and represent hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms;

—$CR_{17}C(OH)R_{22}R_{23}$ where $R_{22}$ and $R_{23}$ are the same or different and represent straight or branched chain lower alkyl having 1–6 carbon atoms, phenyl, pyridyl, straight or branched chain lower alkyl having 1–6 carbon atoms, or phenylalkyl or pyridylalkyl where each alkyl is straight or branched chain lower alkyl having 1–6 carbon atoms and $R_{17}$ is hydrogen, or straight or branched chain lower alkyl having 1–6 carbon atoms;

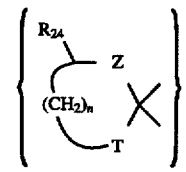

where
n is 0, 1, or 2, $R_{24}$ is hydrogen, aryl, heteroaryl, straight or branched chain lower alkyl having 1–6 carbon atoms, or aryl or heteroaryl straight or branched chain lower alkyl having 1–6 carbon atoms;

Z is methylene, oxygen, $NR_{25}$ or —$CHCONR_{25}$ where $R_{25}$ is hydrogen, straight or branched chain lower alkyl having 1–6 carbon atoms, phenyl, pyridyl, or phenylalkyl or pyridyl alkyl where each alkyl is straight or branched chain lower alkyl having 1–6 carbon atoms; and T is methylene or oxygen.

In addition, the present invention encompasses compounds of Formula II.

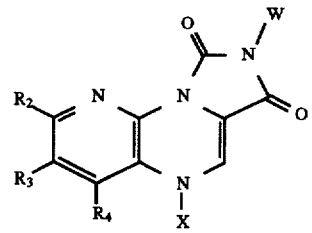

wherein:

$R_3$ and X are the same or different and represent hydrogen or straight or branched chain lower alkyl having 1–6 carbon atoms;

W is phenyl, thienyl, or pyridyl;
  phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

$R_4$ is hydrogen, halogen, straight or branched chain lower alkyl having 1–6 carbon atoms, or straight or branched chain lower alkoxy having 1–6 carbon atoms;

$R_2$ is hydrogen, halogen, hydroxy, amino, 1-indanyl, 4-(thio)chromanyl, 1-(1,2,3,4-tetrahydronaphthyl);
  1-indanyl, 4-(thio)chromanyl, 1-(1,2,3,4-tetrahydronaphthyl), each of which is monosubstituted with halogen, straight or branched chain lower alkyl having 1–6, carbon atoms, or straight or branched chain lower alkoxy having 1–6 carbon atoms;
  $OR_5$, $COR_5$, $CO_2R_5$, $OCOR_5$, or $R_5$, where $R_5$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or
  —$CONR_6R_7$ or —$(CH_2)_nNR_6R_7$ where
  n is 0, 1, or 2;
  $R_6$ is hydrogen, straight or branched chain lower alkyl having 1–6 carbon atoms; and
  $R_7$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or
  $NR_6R_7$ forms a heterocyclic group which is morpholyl, piperidyl, pyrrolidyl, or N-alkyl piperazyl.

The present invention also encompasses compounds of Formula III:

wherein:
  W is phenyl, thienyl, or pyridyl;
    phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;
  $R_1$ and $R_4$ are the same or different and represent hydrogen, halogen, straight or branched chain lower alkyl having 1–6 carbon atoms, or straight or branched chain lower alkoxy having 1–6 carbon atoms; and
  $R_3$ and X are the same or different and represent hydrogen or straight or branched chain lower alkyl having 1–6 carbon atoms.

The present invention also encompasses compounds of Formula IV:

wherein:
  W is phenyl, thienyl, or pyridyl;
    phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;
  E represents oxygen, sulfur, N—H, or N—Me;
  $R_1$ is hydrogen, halogen, straight or branched chain lower alkyl having 1–6 carbon atom, or straight or branched chain lower alkoxy having 1–6 carbon atoms;
  $R_2$ is hydrogen, halogen, hydroxy, amino, 1-indanyl, 4-(thio)chromanyl, 1-(1,2,3,4-tetrahydronaphthyl);
    1-indanyl, 4-(thio)chromanyl, 1-(1,2,3,4-tetrahydronaphthyl), each of which is monosubstituted with halogen, straight or branched chain lower alkyl having 1–6, carbon atoms, or straight or branched chain lower alkoxy having 1–6 carbon atoms;
    $OR_5$, $COR_5$, $CO_2R_5$, $OCOR_5$, or $R_5$, where $R_5$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or
    —$CONR_6R_7$ or —$(CH_2)_nNR_6R_7$ where
    n is 0, 1, or 2;
    $R_6$ is hydrogen, straight or branched chain lower alkyl having 1–6 carbon atoms; and
    $R_7$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or
    $NR_6R_7$ forms a heterocyclic group which is morpholyl, piperidyl, pyrrolidyl, or N-alkyl piperazyl; and
  X represents hydrogen or straight or branched chain lower alkyl having 1–6 carbon atoms.

The present invention also encompasses compounds of Formula V:

wherein:
  W is phenyl, thienyl, or pyridyl;
    phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

E represents oxygen, sulfur, N—H, or N—Me;

$R_2$ is hydrogen, halogen, hydroxy, amino, 1-indanyl, 4-(thio)chromanyl, 1-(1,2,3,4-tetrahydronaphthyl);

1-indanyl, 4-(thio)chromanyl, 1-(1,2,3,4-tetrahydronaphthyl), each of which is monosubstituted with halogen, straight or branched chain lower alkyl having 1–6, carbon atoms, or straight or branched chain lower alkoxy having 1–6 carbon atoms;

$OR_5$, $COR_5$, $CO_2R_5$, $OCOR_5$, or $R_5$, where $R_5$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or —$CONR_6R_7$ or —$(CH_2)_nNR_6R_7$ where n is 0, 1, or 2;

$R_6$ is hydrogen, straight or branched chain lower alkyl having 1–6 carbon atoms; and $R_7$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or $NR_6R_7$ forms a heterocyclic group which is morpholyl, piperidyl, pyrrolidyl, or N-alkyl piperazyl; and $R_4$ and X are the same or different and represent hydrogen or straight or branched chain lower alkyl having 1–6 carbon atoms.

The present invention also encompasses compounds of Formula VI:

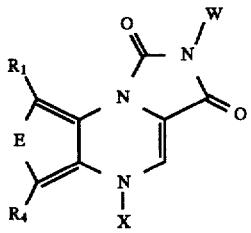

VI wherein:

W is phenyl, thienyl, or pyridyl;

phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

E represents oxygen, sulfur, N—H, or N—Me;

$R_1$ and $R_4$ are the same or different and represent hydrogen, halogen, straight or branched chain lower alkyl having 1–6 carbon atoms, or straight or branched chain lower alkoxy having 1–6 carbon atoms; and X represents hydrogen or straight or branched chain lower alkyl having 1–6 carbon atoms.

The present invention also encompasses compounds of general formula VII:

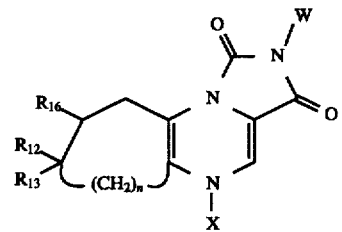

VII wherein:

n is 0, 1, or 2;

$R_{12}$ and $R_{13}$ are the same or different and represent hydrogen or straight or branched chain lower alkyl having 1–6 carbon atoms;

$R_{16}$ is hydrogen, straight or branched chain lower alkyl having 1–6 carbon atoms, phenyl, pyridyl, or phenylalkyl or pyridylalkyl where each alkyl is straight or branched chain lower alkyl having 1–6 carbon atoms;

W is phenyl, thienyl, or pyridyl;

phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms; and X represents hydrogen or straight or branched chain lower alkyl having 1–6 carbon atoms.

The present invention also encompasses compounds of general formula VIII:

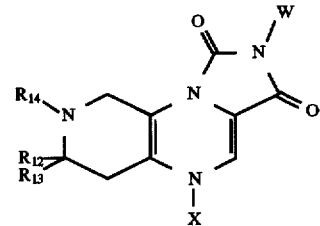

VIII where $R_{12}$ and $R_{13}$ are the same or different and represent hydrogen or straight or branched chain lower alkyl having 1–6 carbon atoms;

W is phenyl, thienyl, or pyridyl; phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

$R_{14}$ is hydrogen, phenyl, pyridyl, straight or branched chain lower alkyl having 1–6 carbon atoms, phenylalkyl or pyridylalkyl where each alkyl is straight or branched chain lower alkyl having 1–6 carbon atoms; aminoalkyl where the alkyl is a straight or branched chain lower alkyl having 1–6 carbon atoms, or mono or dialkyl aminoalkyl where each alkyl is a straight or branched chain lower alkyl having 1–6 carbon atoms;

1-indanyl, 4-(thio)chromanyl, 1-(1,2,3,4-tetrahydronaphthyl);

1-indanyl, 4-(thio)chromanyl, 1-(1,2,3,4-tetrahydronaphthyl) each of which is monosubstituted with halogen, straight or branched chain lower, alkyl having 1–6 carbon atoms, or straight or branched chain lower alkoxy having 1–6 carbon atoms;

—COR$_{15}$ or —SO$_2$R$_{15}$ where R$_{15}$ is straight or branched chain lower alkyl having 1–6 carbon atoms, phenyl, pyridyl, phenylalkyl or pyridylalkyl where each alkyl is straight or branched chain lower alkyl having 1–6 carbon atoms, or phenylalkoxy or pyridylalkoxy where each alkoxy is straight or branched chain lower alkoxy having 1–6 carbon atoms; and X represents hydrogen or straight or branched chain lower alkyl having 1–6 carbon atoms.

The present invention also encompasses compounds of general formula IX:

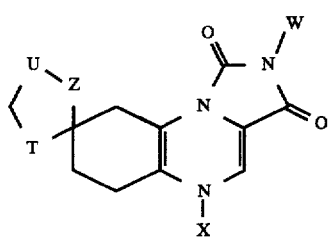

where

W is phenyl, thienyl, or pyridyl;

phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

Z is methylene, oxygen or NR$_{25}$ where R$_{25}$ is hydrogen, straight or branched chain lower alkyl having 1–6 carbon atoms, phenyl, pyridyl, or phenylalkyl or pyridylalkyl where each alkyl is straight or branched chain lower alkyl having 1–6 carbon atoms;

T is methylene or oxygen;

U is methylene or carbonyl; and

X represents hydrogen or straight or branched chain lower alkyl having 1–6 carbon atoms.

Non-toxic pharmaceutical salts include salts of acids such as hydrochloric, phosphoric, hydrobromic, sulfuric, sulfinic, formic, toluene sulfonic, hydroiodic, acetic and the like. Those skilled in the art will recognize a wide variety of non-toxic pharmaceutically acceptable addition salts.

Figure 1B:
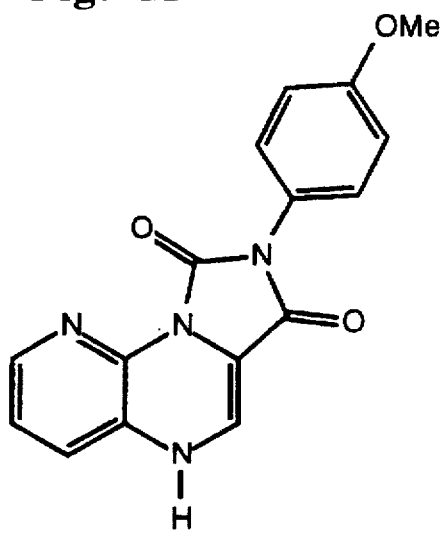
Figure 1C:
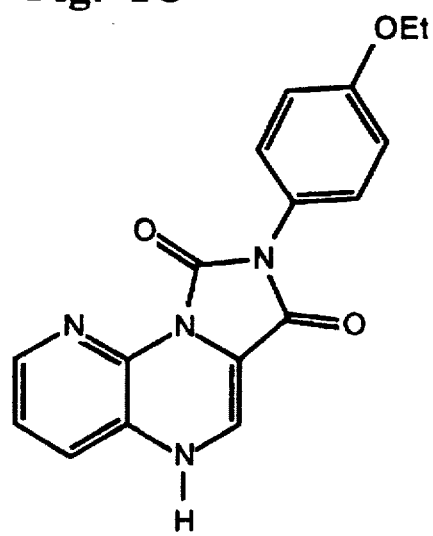

Representative compounds of the present invention which are encompassed by Formula I, include, but are not limited to the compounds in FIG. 1 and their pharmaceutically acceptable salts. The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

By lower alkyl in the present invention is meant straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By lower alkoxy in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By halogen in the present invention is meant fluorine, bromine, chlorine, and iodine.

By N-alkylpiperazyl in the invention is meant radicals of the formula:

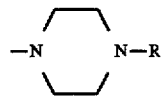

where R is a straight or branched chain lower alkyl as defined above.

By 4-(thio)chromanyl is meant a radical of the formula:

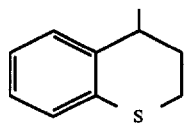

The pharmaceutical utility of compounds of this invention are indicated by the following assay for GABAa receptor activity.

Assays are carried out as described in Thomas and Tallman (J. Bio. Chem. 156:9838–9842, J. Neurosci. 3:433–440, 1983). Rat cortical tissue is dissected and homogenized in 25 volumes (w/v) of 0.05M Tris HCl buffer (pH 7.4 at 4° C.). The tissue homogenate is centrifuged in the cold (4°) at 20,000×g for 20'. The supernatant is decanted and the pellet is rehomogenized in the same volume of buffer and again centrifuged at 20,000×g. The supernatant is decanted and the pellet is frozen at −20° C. overnight. The pellet is then thawed and rehomogenized in 25 volume (original wt/vol) of buffer and the procedure is carried out twice. The pellet is finally resuspended in 50 volumes (w/vol of 0.05M Tris HCl buffer (pH 7.4 at 40° C.).

Incubations contain 100 ml of tissue homogenate, 100 ml of radioligand 0.5 nM ($^3$H-RO15-1788 [$^3$H-Flumazenil] specific activity 80 Ci/mmol), drug or blocker and buffer to a total volume of 500 ml. Incubations are carried for 30 min at 4° C. then are rapidly filtered through GFB filters to separate free and bound ligand. Filters are washed twice with fresh 0.05M Tris HCl buffer (pH 7.4 at 4° C.) and counted in a liquid scintillation counter. 1.0 mM diazepam is added to some tubes to determine nonspecific binding. Data are collected in triplicate determinations, averaged and % inhibition of total specific binding is calculated. Total Specific Binding=Total–Nonspecific. In some cases, the amounts of unlabeled drugs is varied and total displacement curves of binding are carried out. Data are converted to a form for the calculation of IC$_{50}$ and Hill Coefficient (nH). Data for the compounds of this invention are listed in Table I.

TABLE I

| Compound Number[1] | IC$_{50}$(uM) |
|---|---|
| 1 | 0.010 |
| 5 | 0.009 |
| 8 | 0.020 |

[1]Compound numbers relate to compounds shown in FIG. 1.

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinyl-pyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitor or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water. Ringer's solution and isotonic sodium chloride solution, in addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Schemes I and II. Those having skill in the art will recognize that the starting materials may be varied and additional steps employed to produce compounds encompassed by the present invention, as demonstrated by the following examples.

$R_2$ is hydrogen, halogen, hydroxy, amino, 1-indanyl, 4-(thio)chromanyl, 1-(1,2,3,4-tetrahydronaphthyl);

1-indanyl, 4-(thio)chromanyl, 1-(1,2,3,4-tetrahydronaphthyl), each of which is monosubstituted with halogen, straight or branched chain lower alkyl having 1–6, carbon atoms, or straight or branched chain lower alkoxy having 1–6 carbon atoms;

$OR_5$, $COR_5$, $CO_2R_5$, $OCOR_5$, or $R_5$, where $R_5$ is hydrogen, phenyl, pyridyl, straight or branched chain lower alkyl having 1–6 is straight or branched chain lower alkyl having 1–6 carbon atoms;

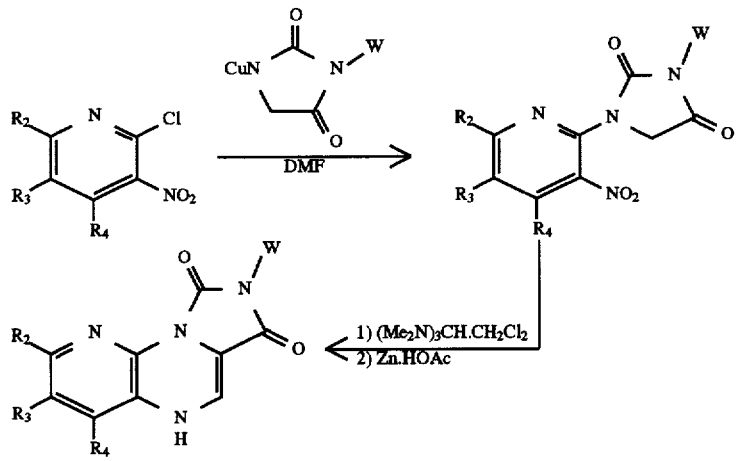

Scheme 1

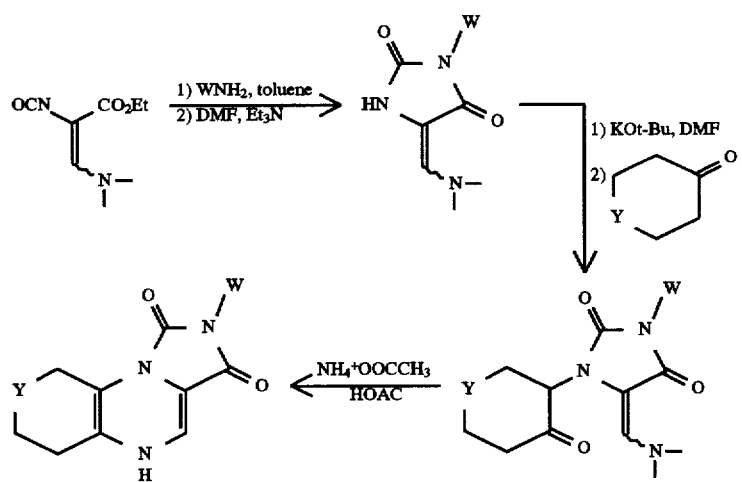

Scheme II wherein:

W is phenyl, thienyl, or pyridyl;
phenyl, thienyl, or pyridyl, each of which may be mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms;

—$CONR_6R_7$ or —$(CH_2)_nNR_6R_7$ where n is 0, 1, or 2;

$R_6$ is hydrogen, straight or branched chain lower alkyl having 1–6 carbon atoms; and $R_7$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms; or NR$_6$R$_7$ forms a heterocyclic group which is morpholyl, piperidyl, pyrrolidyl, or N-alkyl piperazyl; or C(OH)R$_{10}$R$_{11}$ where R$_{10}$ and R$_{11}$ are the same or different and represent straight or branched chain lower alkyl having 1–6 carbon atoms, phenyl, or phenylalkyl where each alkyl is straight or branched chain lower alkyl having 1–6 carbon atoms;

R$_3$ is hydrogen or straight or branched chain lower alkyl having 1–6 carbon atoms;

R$_4$ is hydrogen, halogen, straight or branched chain lower alkyl having 1–6 carbon atoms, or straight or branched chain lower alkoxy having 1–6 carbon atoms; and Y is N—R$_{14}$ where R$_{14}$ is hydrogen, phenyl, pyridyl, straight or branched chain lower alkyl having 1–6 carbon atoms, phenylalkyl or pyridylalkyl where each alkyl is straight or branched chain lower alkyl having 1–6 carbon atoms;

aminoalkyl where the alkyl is a straight or branched chain lower alkyl having 1–6 carbon atoms, or mono or dialkyl aminoalkyl where each alkyl is a straight or branched chain lower alkyl having 1–6 carbon atoms;

1-indanyl, 4-(thio)chromanyl, 1-(1,2,3,4-tetrahydronaphthyl);

1-indanyl, 4-(thio)chromanyl, 1-(1,2,3,4-tetrahydronaphthyl) each of which is monosubstituted with halogen, straight or branched chain lower alkyl having 1–6 carbon atoms, or straight or branched chain lower alkoxy having 1–6 carbon atoms;

—COR$_{15}$ or —SO$_2$R$_{15}$ where R$_{15}$ is straight or branched chain lower alkyl having 1–6 carbon atoms, phenyl, pyridyl, phenylalkyl or pyridylalkyl where each alkyl is straight or branched chain lower alkyl having 1–6 carbon atoms, or phenylalkoxy or pyridylalkoxy where each alkoxy is straight or branched chain lower alkoxy having 1–6 carbon atoms;

—CO—, —CR$_{17}$OR$_{16}$, —CR$_{17}$COR$_{16}$, —CR$_{17}$CO$_2$R$_{16}$, —CR$_{17}$OCOR$_{16}$, and —CR$_{16}$R$_{17}$, where R$_{16}$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms, and R$_{17}$ is hydrogen, or straight or branched chain lower alkyl having 1–6 carbon atoms;

—CR$_{17}$CONR$_{18}$R$_{19}$ or —CR$_{17}$(CH$_2$)$_n$NR$_{18}$R$_{19}$ where n is 0,1, or 2, and R$_{17}$ and R$_{18}$ are the same or different and represent hydrogen, straight or branched chain lower alkyl having 1–6 carbon atoms, and R$_{19}$ is hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms, or NR$_{18}$R$_{19}$ together forms a heterocyclic group which is morpholyl, piperidyl, pyrrolidyl, or N-alkylpiperazyl;

—CR$_{17}$NR$_{20}$CO$_2$R$_{21}$ where

R$_{17}$ is hydrogen, straight or branched chain lower alkyl having 1–6 carbon atoms, and R$_{20}$ and R$_{21}$ are the same or different and represent hydrogen, phenyl, pyridyl, straight or branched chain lower alkyl having 1–6 carbon atoms, or phenylalkyl or pyridylalkyl where each alkyl is straight or branched chain lower alkyl having 1–6 carbon atoms;

—CR$_{17}$C(OH)R$_{22}$R$_{23}$ where

R$_{22}$ and R$_{23}$ are the same or different and represent straight or branched chain lower alkyl having 1–6 carbon atoms, phenyl, pyridyl, straight or branched chain lower alkyl having 1–6 carbon atoms, or phenylalkyl or pyridylalkyl where each alkyl is straight or branched chain lower alkyl having 1–6 carbon atoms and R$_{17}$ is hydrogen, or straight or branched chain lower alkyl having 1–6 carbon atoms;

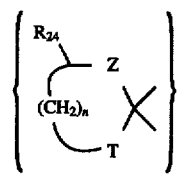

where n is 0, 1, or 2,

R$_{24}$ is hydrogen, aryl, heteroaryl, straight or branched chain lower alkyl having 1–6 carbon atoms, or aryl or heteroaryl straight or branched chain lower alkyl having 1–6 carbon atoms;

Z is methylene, oxygen, NR$_{25}$ or —CHCONR$_{25}$ where R$_{25}$ is hydrogen, straight or branched chain lower alkyl having 1–6 carbon atoms, phenyl, pyridyl, or phenylalkyl or pyridyl alkyl where each alkyl is straight or branched chain lower alkyl having 1–6 carbon atoms; and T is methylene or oxygen.

Those having skill in the art will recognize that the starting materials may be varied and additional steps employed to produce compounds encompassed by the present invention, as demonstrated by the following examples. In some cases protection of certain reactive functionalities may be necessary to achieve some of the above transformations. In general the need for such protecting groups will be apparent to those skilled in the art of organic synthesis as well as the conditions necessary to attach and remove such groups.

The invention is illustrated further by the following examples which are not to be construed as limiting the invention in scope or spirit to the specific procedures described in them.

Example I

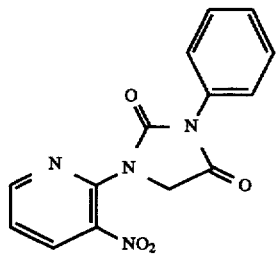

To a solution containing 3-Phenyl-imidazoline-2,4-dione (1.76 g) in dimethylformamide (200 mL) at 0° C. was added 1M potassium tert-butoxide (10 mL) in tetrahydrofuran.

After 5 min Copper (I) Iodide (1.9 gm) was added and the solution was allowed to stir at room temperature for 15 min. 2-Chloro-3-nitropyridine (2.21 g) was then added and the mixture was heated under nitrogen at 150° C. for 5 h. The mixture was cooled to room temperature and then partitioned between saturated ammonium chloride (250 mL) and ethyl acetate (200 mL) The organic layer was washed successively with saturated ammonium chloride (2×), water (2×) and then dried with sodium sulfate. The solvent was removed at reduced pressure and purified by column chromatography to yield 1-(3-Nitropyridyl)-3-phenyl-imidazoline-2,4(1H,3H)-dione as a white solid.

Example II

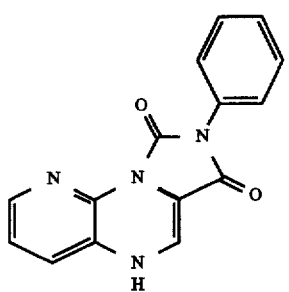

(Compound 1)

To a solution of 1-(3-Nitropyridyl)-3-phenyl-imidazoline-2,4,(1H,3H)-dione (500 mg) in methylene chloride (20 mL) was added trisdimethylaminomethane (1 mL). The solution was allowed to sit at room temperature for 1 h followed by removal of solvent at reduced pressure. The resulting red oil was dissolved in acetic acid (25 mL) and added to a suspension of zinc dust (1.5 g) in acetic acid (50 mL). The mixture was heated to reflux for 5 min and then cooled to room temperature over a 45 min period. The reaction was filtered through celite and the acetic acid was removed at reduced pressure. Water (25 mL) was added and the resulting yellow solid was collected and washed with ethanol to yield 2-Phenyl-imidazo[1,5,a]pyrido[3,2-e]pyrazine-1,3 (2H,5H)-dione (Compound 1). m.p. 350° C. (dec.)

Example III

The following compounds were prepared essentially according to the procedures set forth in Examples I-II.

a) 2-(2-Fluorophenyl)-imidazo[1,5,a]pyrido[3,2-e]pyrazine-2,3(2H,5H)-dione (Compound 2).

b) 2-(2-Fluorophenyl-4-ethoxyphenyl)-imidazo[1,5,a]pyrido[3,2-e]pyrazine-2,3(2H,5H)-dione (Compound 3).

c) 2-(4-Methylphenyl)-imidazo[1,5,a]pyrido[3,2-e]pyrazine-2,3(2H,5H)-dione (Compound 4).

d) 2-(4-Methoxyphenyl)-imidazo[1,5,a]pyrido[3,2-e]pyrazine-2,3(2H,5H)-dione (Compound 5).

e) 2-(4-Ethylphenyl)-imidazo[1,5,a]pyrido[3,2-e]pyrazine-2,3(2H,5H)-dione (Compound 6).

f) 2-(4-Ethylphenyl)-imidazo[1,5,a]pyrido[3,2-e]pyrazine-2,3(2H,5H)-dione Compound 7).

g) 2-(4-Ethoxyphenyl)-imidazo[1,5,a]pyrido[3,2-e]pyrazine-2,3(2H,5H)-dione (Compound 8).

h) 2-(3-Methoxyphenyl)-imidazo[1,5,a]pyrido[3,2-e]pyrazine-2,3(2H,5H)-dione (Compound 9).

i) 2-(4-n-propyloxyphenyl)-imidazo[1,5,a]pyrido[3,2-e]pyrazine-2,3(2H, 5H)-dione (Compound 10).

j) 2-(3-Ethoxyphenyl)-imidazo[1,5,a]pyrido[3,2-e]pyrazine-2,3(2H,5H)-dione (Compound 11).

k) 2-(4-Isopropoxyphenyl)-imidazo[1,5,a]pyrido[3,2-e]pyrazine-2,3(2H,5H)-dione (Compound 12).

l) 2-(4-Chlorophenyl)-imidazo[1,5,a]pyrido[3,2-e]pyrazine-2,3(2H,5H)-dione (Compound 13).

m) 2-(3-Chlorophenyl)-imidazo[1,5,a]pyrido[3,2-e]pyrazine-2,3(2H,5H)-dione (Compound 14).

n) 2-(4-Hydroxyphenyl)-imidazo[1,5,a]pyrido[3,2-e]pyrazine-2,3(2H,5H)-dione (Compound 15).

o) 5-N-Methyl-2-(4-Ethoxyphenyl)-imidazo[1,5,a]pyrido[3,2-e]pyrazine-2,3(2H,5H)-dione (Compound 16).

p) 2-(4-Propylphenyl)-imidazo[1,5,a]pyrido[3,2-e]pyrazine-2,3(2H,5H)-dione (Compound 17).

q) 7-Methyl-2-(3-methoxyphenyl)-imidazo[1,5,a]pyrido[3,2-e]pyrazine-2,3(2H,5H)-dione (Compound 18).

r) 7-Methyl-2-phenyl-imidazo[1,5,a]pyrido[3,2-e]pyrazine-2,3(2H,5H)-dione Compound 19).

s) 8-Chloro-2-(3-methoxyphenyl)-imidazo[1,5,a]pyrido[3,2-e]pyrazine-2,3(2H,5H)-dione (Compound 20).

Example IV

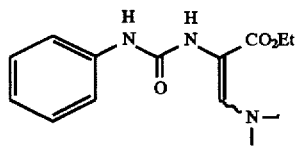

To a solution of Ethyl 2-isocyanato-3-(dimethylamino)-propenoate (5.52 g) in toluene (250 mL) was added aniline (2.79 g). The reaction was stirred at room temperature for 30 min. The resulting solid was collected and dried to yield N-(1-Carboethoxy-2-dimethylaminovinyl)-N'-phenyl urea as a white solid.

Example V

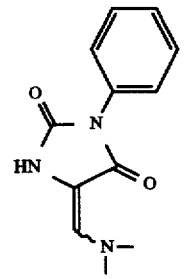

To a solution of Ethyl-2-N-3-(dimethylamino)-2-propenoate-N'-phenyl urea (2.31 g) in dimethylformamide (50 mL) was added triethylamine (0.1 mL). The solution was heated to 80° C. for 1 h cooled to room temperature and then partitioned between water (200 mL) and Ethyl Acetate (200 mL). The organic phase was dried over sodium sulfate and the solvent was removed at reduced pressure to yield a reddish oil. Purification by column chromatography yielded 3-Phenyl-5-(dimethylaminomethylene)-imidazoline-2,4-dione as an off white solid.

Example VI (Compound 21)

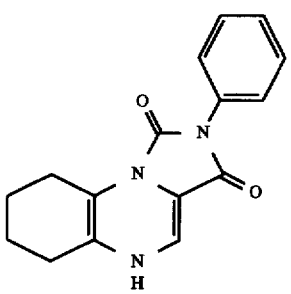

To a solution of 3-Phenyl-5-(dimethylaminomethylene)-imidazoline-2,4-dione (1.3 g) in dimethylformamide (20 mL) at 0° C. was added 1M potassium tert-butoxide (5 mL) in tetrahydrofuran. After 5 min 2-Chlorocycloxeanone (700 mg) was added and the mixture was stirred for 30 min. Acetic acid (1 mL) was added and the solvent was removed at reduced pressure. To the resulting residue was added ammonium acetate (10 gm) and acetic acid (25 ml) and the mixture was heated to reflux for 4 h. The solvent was removed at reduced pressure and water (50 mL) was added. The resulting solid was collected, washed with methanol and dried to yield 2-Phenyl-6,7,8,9-tetrahydro-imidazo[1,5,a]quinoxaline-1,3(2H,5H)-dione (Compound 21) as an off white solid, m.p. 236°–240° C.

Example VII

The following compounds were prepared essentially according to the procedures described in Examples IV–VI.

a) 2-(4-Methylphenyl)-6,7,8,9-tetrahydro-imidazo[1,5,a]quinoxaline-1,3(2H,5H)-dione (Compound 22).
b) 2-(4-Ethylphenyl )-6,7,8,9-tetrahydro-imidazo[1,5,a]quinoxaline-1,3(2H,5H)-dione (Compound 23).
c) 2-(4-Chlorophenyl)-6,7,8,9-tetrahydro-imidazo[1,5,a]quinoxaline-1,3(2H,5H)-dione (Compound 24).
d) 2-(4-Methoxyphenyl)-6,7,8,9-tetrahydro-imidazo[1,5,a]quinoxaline-1,3(2H,5H)-dione (Compound 25).
e) 2-(2-Fluorophenyl)-6,7,8,9-tetrahydro-imidazo[1,5,a]quinoxaline-1,3(2H,5H)-dione (Compound 26).
f) 2-(4-Ethoxyphenyl)-6,7,8,9-tetrahydro-imidazo[1,5,a]quinoxaline-1,3(2H,5H)-dione (Compound 27).
g) 2-(3-Methoxyphenyl)-6,7,8,9-tetrahydro-imidazo[1,5,a]quinoxaline-1,3(2H,5H)-dione (Compound 28).
h) 2-(3-Ethoxyphenyl)-6,7,8,9-tetrahydro-imidazo[1,5,a]quinoxaline-1,3(2H,5H)-dione (Compound 29).
i) 2-(3-Chlorophenyl)-6,7,8,9-tetrahydro-imidazo[1,5,a]quinoxaline-1,3(2H,5H)-dione (Compound 30).
j) 2-(4-n-Propyloxyphenyl)-6,7,8,9-tetrahydro-imidazo[1,5,a]quinoxaline-1,3(2H,5H)-dione (compound 31).
k) 2-(4-Propylphenyl)-6,7,8,9-tetrahydro-imidazo[1,5,a]quinoxaline-1,3(2H,5H)-dione (Compound 32).
l) 2-(4-Isopropoxyphenyl)-6,7,8,9-tetrahydro-imidazo[1,5,a]quinoxaline-1,3(2H,5H)-dione (Compound 33).
m) 5-N-Methyl-2-phenyl-6,7,8,9-tetrahydro-imidazo[1,5,a]quinoxaline-1,3(2H,5H)-dione (Compound 34).
n) 5-N-Methyl-2-(4-ethoxyphenyl)-6,7,8,9-tetrahydro-imidazo[1,5,a]quinoxaline-1,3(2H,5H)-dione (Compound 35).
o) 2-(2-Fluoro-4-ethoxyphenyl)-6,7,8,9-tetrahydro-imidazo[1,5,a]quinoxaline-1,3(2H,5H)-dione (Compound 36).
p) 2-(2-Fluoro-4-methylphenyl)-6,7,8,9-tetrahydro-imidazo[1,5,a]quinoxaline-1,3(2H,5H)-dione (Compound 37).

Example VIII

The following compounds were also prepared essentially according to the procedures set forth in Examples I–VI.

a) 2-Phenyl-imidazo[1,5,a]pyrido[4,3-e]pyrazine-2,3(2H,5H)-dione (Compound 38).
b) 2-(4-Ethoxyphenyl)-imidazo[1,5,a]pyrido[4,3-e]pyrazine-2,3(2H,5H)-dione (Compound 39).
c) 2-(4-Ethoxyphenyl)-imidazo[1,5,a]thieno[3,2-e]pyrazine-2,3(2H,5H)-dione (Compound 40).
d) 2-(4-Ethoxyphenyl)-imidazo[1,5,a]thieno[2,3-e]pyrazine-2,3(2H,5H)-dione (Compound 41).
e) 2-(4-Ethoxyphenyl)-imidazo[1,5,a]thieno[3,4-e]pyrazine-2,3(2H,5H)-dione (Compound 42).
f) 2-(4-Ethoxyphenyl)-cyclopent(e)-imidazo[1,5,a]pyrazine-2,3(2H,5H)-dione (Compound 43).
g) 2-(4-Ethoxyphenyl)-cyclohept(e)-imidazo[1,5,a]pyrazine-2,3(2H,5H)-dione (Compound 44).
h) 8-Benzyl-2-(4-methoxyphenyl)-6,7,8,9-tetrahydro-imidazo[1,5,a]pyrido[4,3-e]pyrazine-2,3(2H,5H)-dione (Compound 45).

The invention and the manner and process of making and using it, are now described in such full, clear, concise and exact terms as to enable any person skilled in the an to which it pertains, to make and use the same. It is to be understood that the foregoing describes preferred embodiments of the present invention and that modifications may be made therein without departing front the spirit or scope of the present invention as set forth in the claims. To particularly point out and distinctly claim the subject matter regarded as invention, the following claims conclude this specification.

What is claimed is:

1. A compound of the formula:

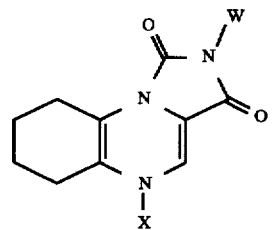

or the pharmaceutically acceptable non-toxic salts thereof wherein:

X is hydrogen or lower alkyl having 1–6 carbon atoms; and

W is phenyl, thienyl, or pyridyl, each of which is optionally mono or disubstituted with halogen, hydroxy, straight or branched chain lower alkyl having 1–6 carbon atoms, amino, mono or dialkylamino where each alkyl is straight or branched chain lower alkyl having 1–6 carbon atoms, or straight or branched chain lower alkoxy having 1–6 carbon atoms.

2. A compound according to claim 1, wherein W is phenyl substituted with one or two groups selected from Methyl; Ethyl; Chloro; Methoxy; Fluoro; Ethoxy; n-Propyloxy; Propyl; and Isopropoxy.

3. A compound according to claim 2, wherein X is hydrogen.

4. A compound according to claim 1, wherein X is methyl and W is selected from the group consisting of Phenyl;

Ethoxyphenyl;

Phenyl disubstituted with fluoro and ethoxy; and

Phenyl disubstituted with fluoro and methyl.

5. A compound according to claim 1, which is 2-Phenyl-6,7,8,9-tetrahydro-imidazo[1,5,a]quinoxaline-1,3(2H,5H)-dione.

6. A compound according to claim 1, which is 2-(4-Methylphenyl)-6,7,8,9-tetrahydro-imidazo[1,5,a]quinoxaline-1,3(2H,5H)-dione.

7. A compound according to claim 1, which is 2-(4-Ethylphenyl)-6,7,8,9-tetrahydro-imidazo[1,5,a]quinoxaline-1,3(2H,5H)-dione.

8. A compound according to claim 1, which is 2-(4-Chlorophenyl)-6,7,8,9-tetrahydro-imidazo[1,5,a]quinoxaline-1,3(2H,5H)-dione.

9. A compound according to claim 1, which is 2-(4-Methoxyphenyl)-6,7,8,9-tetrahydro-imidazo[1,5,a]quinoxaline-1,3(2H,5H)-dione.

10. A compound according to claim 1, which is 2-(2-Fluorophenyl)-6,7,8,9-tetrahydro-imidazo[1,5,a]quinoxaline-1,3(2H,5H)-dione.

11. A compound according to claim 1, which is 2-(4-Ethoxyphenyl)-6,7,8,9-tetrahydro-imidazo[1,5,a]quinoxaline-1,3(2H,5H)-dione.

12. A compound according to claim 1 which is 2-(3-Methoxyphenyl)-6,7,8,9-tetrahydro-imidazo[1,5,a]quinoxaline-1,3(2H,5H)-dione.

13. A compound according to claim 1, which is 2-(3-Ethoxyphenyl)-6,7,8,9-tetrahydro-imidazo[1,5,a]quinoxaline-1,3(2H,5H)-dione.

14. A compound according to claim 1, which is 2-(3-Chlorophenyl)-6,7,8,9-tetrahydro-imidazo[1,5,a]quinoxaline-1,3(2H,5H)-dione.

15. A compound according to claim 1, which is 2-(4-n-Propyloxyphenyl)-6,7,8,9-tetrahydro-imidazo[1,5,a]quinoxaline-1,3(2H,5H)-dione.

16. A compound according to claim 1, which is 2-(4-Propylphenyl)-6,7,8,9-tetrahydro-imidazo[1,5,a]quinoxaline-1,3(2H,5H)-dione.

17. A compound according to claim 1, which is 2-(4-Isopropoxyphenyl)-6,7,8,9-tetrahydro-imidazo[1,5,a]quinoxaline-1,3(2H,5H)-dione.

18. A compound according to claim 1, which is 5-N-Methyl-2-phenyl-6,7,8,9-tetrahydro-imidazo[1,5,a]quinoxaline-1,3(2H,5H)-dione.

19. A compound according to claim 1, which is 5-N-Methyl-2-(4-ethoxyphenyl)-6,7,8,9-tetrahydro-imidazo[1,5,a]quinoxaline-1,3(2H,5H)-dione.

20. A compound according to claim 1, which is 2-(2-Fluoro-4-ethoxyphenyl)-6,7,8,9-tetrahydro-imidazo[1,5,a]quinoxaline-1,3(2H,5H)-dione.

21. A compound according to claim 1, which is 2-(2-Fluoro-4-methylphenyl)-6,7,8,9-tetrahydro-imidazo[1,5,a]quinoxaline-1,3(2H,5H)-dione.

* * * * *